United States Patent
Kuznetsov et al.

(10) Patent No.: US 11,804,311 B1
(45) Date of Patent: Oct. 31, 2023

(54) USE AND COORDINATION OF HEALTHCARE INFORMATION WITHIN LIFE-LONG CARE TEAM

(71) Applicant: COMMURE, INC., Palo Alto, CA (US)

(72) Inventors: Eugene Kuznetsov, Cambridge, MA (US); Diede Van Lamoen, San Francisco, CA (US)

(73) Assignee: COMMURE, INC., Palo Alto, CA (US)

( * ) Notice: Subject to any disclaimer, the term of this patent is extended or adjusted under 35 U.S.C. 154(b) by 1,277 days.

(21) Appl. No.: 16/126,481

(22) Filed: Sep. 10, 2018

Related U.S. Application Data

(60) Provisional application No. 62/565,540, filed on Sep. 29, 2017.

(51) Int. Cl.
*G16H 80/00* (2018.01)
*G16H 10/60* (2018.01)

(52) U.S. Cl.
CPC ................ *G16H 80/00* (2018.01); *G16H 10/60* (2018.01)

(58) Field of Classification Search
CPC ................ G16H 80/00; G16H 10/60
See application file for complete search history.

(56) References Cited

U.S. PATENT DOCUMENTS

| | | | |
|---|---|---|---|
| 2006/0173708 A1* | 8/2006 | Vining et al. |
| 2010/0088121 A1* | 4/2010 | Shih et al. |
| 2010/0191546 A1* | 7/2010 | Kanamarlapudi et al. |
| 2010/0223073 A1* | 9/2010 | Nearman et al. |
| 2014/0058754 A1* | 2/2014 | Wild |
| 2016/0125152 A1* | 5/2016 | Higgs |
| 2018/0122499 A1* | 5/2018 | Austin et al. |
| 2019/0005200 A1* | 1/2019 | Zimmerman et al. |
| 2019/0087544 A1* | 3/2019 | Peterson |

* cited by examiner

*Primary Examiner* — Michael Tomaszewski
*Assistant Examiner* — William T. Monticello
(74) *Attorney, Agent, or Firm* — Sterne, Kessler, Goldstein & Fox P.L.L.C.

(57) ABSTRACT

Managing healthcare information includes a first healthcare professional subscribing to a subset of medical information for a patient in a healthcare information framework having a datastore containing electronic health records for the patient, the first healthcare professional being a member of a life-long care team for the patient that includes all care teams encountered by the patient at any time, a second healthcare professional posting medical information about the patient in the healthcare information framework, pushing, in real time or near real time, the medical information to at least one server that is coupled to the datastore, and the at least one server causing the first healthcare professional to automatically receive the subset of the medical information based on the first healthcare professional subscribing to the subset of the medical information. The second healthcare professional may be invited based on analysis of data in the datastore.

22 Claims, 12 Drawing Sheets

USE AND COORDINATION OF HEALTHCARE INFORMATION WITHIN LIFE-LONG CARE TEAM

CROSS-REFERENCE TO RELATED APPLICATIONS

This application claims priority to U.S. Prov. App. No. 62/565,540, filed on Sep. 29, 2017, and entitled "USE AND COORDINATION OF HEALTHCARE INFORMATION WITHIN LIFE-LONG CARE TEAM", which is incorporated herein by reference.

TECHNICAL FIELD

This application is directed to the field of healthcare information processing, and more particularly to the field of use and coordination of healthcare information within a life-long care team.

BACKGROUND OF THE INVENTION

Healthcare spending in the US has reached 18% of the GDP, making the healthcare industry the fifth largest worldwide economy if taken as a separate entity. Billions of dollars are spent annually to digitize healthcare; numerous legislative acts prescribe a prominent use of EHR (Electronic Health Records) by healthcare organizations and professionals. In spite of these efforts, the country has seen a net loss of healthcare efficiency. The US spends by far the most on healthcare per capita among all countries (approx. $10,000 per year) but doesn't lead the world in either healthcare outcomes or life expectancy (currently about 78.7 years, 1.5 years below the average OECD life expectancy).

One of the most unexpected consequences of computerization of healthcare is a massive overload experienced by physicians: on average, almost 60% of physicians' time is spent working on a computer instead of seeing patients. If this trend persists and the efficiency of healthcare does not improve significantly, experts project a shortfall of 90,000 physicians within less than 10 years. Additionally, burnout among physicians due to inefficiencies of the healthcare system is leading to accelerated attrition and an erosion of empathy, resulting in weakened improvement across outcomes.

At the root of a broken computerized healthcare system lies a problem of technology platforms and data. Healthcare professionals, much less patients, do not have a unified/quantified view of information (for example, Epic EHR records don't carry over to those stored in the Cerner or Allscripts systems). EHRs do not talk to each other, often fail to interface with other practice-focused software, and often intentionally stymie access to their data by third-party developers and other entities. Training, implementation, cost, and complexity are substandard. Additionally, many important types of information aren't even captured in the EHR system, for example, genetic data, exercise information, diet, HRAs/biometrics, etc. The absence of unified and vital information leads to additional health risks for the patient. Escalation of care is poor, too; thus, patients unintentionally inflict high costs on the healthcare system, for example, by visiting an ER (Emergency Room) instead of taking advantage of telemedicine, urgent care, or in-network options. This occurs largely due to the failure of these disparate elements of the healthcare system to communicate with each other.

Healthcare professionals (physicians, nurses, technicians, etc.) experience extreme tech fatigue, in large part due to the shift of burden of software upkeep to the medical professionals. Electronic Health Records data management and software applications are built on ancient technology stacks, have outdated and complex user interfaces and require the professional to engage on the terms of the EHR billing system. Providers often feel that patient care is suffering due to the additional time needed to record notes and information in the EHR and are frustrated that the providers need to acquire additional resources e.g., scribes, to minimize workflow disruption.

Another major challenge of the healthcare system is an insufficient level of communications and care coordination between different entities. As a patient is handed-off between different doctors and institutions, there is a constant theme of nobody talking to each other. Even within a hospital where an inpatient care is provided in the most condensed form, it is not uncommon that communication among a care team is spotty, with one doctor not being aware of what the other has done or concluded.

The infrastructure that powers healthcare today has no contemplation of communication around a patient. Ideally, each person that touches a patient's care should be able to actively communicate with anybody else relevant who has previously been involved, regardless of the respective care institutions of the providers. Analogously, any data created through patient's encounters with any care team should be available, selectively or completely, to any other care team with on-call capabilities to enable constructive communications about a patient's past or existing condition and diagnosis.

Accordingly, it is desirable to create a patient-centric healthcare coordination system with unified, timely and consistent access to all patient data across care teams, extensive communication between all healthcare professionals providing care to the patient, and intelligent escalation of care.

SUMMARY OF THE INVENTION

According to the system described herein, managing healthcare information includes a first healthcare professional subscribing to a subset of medical information for a patient in a healthcare information framework having a datastore containing electronic health records for the patient, the first healthcare professional being a member of a life-long care team for the patient that includes all care teams encountered by the patient at any time, a second healthcare professional posting medical information about the patient in the healthcare information framework, pushing, in real time or near real time, the medical information to at least one server that is coupled to the datastore, and the at least one server causing the first healthcare professional to automatically receive the subset of the medical information based on the first healthcare professional subscribing to the subset of the medical information. The first healthcare professional subscribing to the subset of medical information may be subject to authorization and appropriate credentials. The electronic health records provided in the datastore may be life-long electronic health records. Subscriptions to the subset of medical information may be filtered based on time period, patient ID, event type, and/or specific parameters or thresholds of data associated with subscribed events. Managing healthcare information may also include a realtime or near realtime event bus receiving an event in response to the subset of medical information being posted by the second healthcare professional, wherein the event bus interacts with the server to cause the first healthcare professional to automatically receive the subset of the medical information. The subset of medical information may correspond to a data change event. The data change event may correspond to arrival of results of a diagnostic laboratory test. The subset of medical information may correspond to a new care team event. The new care team event may be caused by admission of the patient to a healthcare facility. The subset of medical information may correspond to a medical appointment event.

According further to the system described herein, managing healthcare information includes a first healthcare professional posting new medical information for a patient in a healthcare information framework having a datastore containing electronic health records for the patient, the first healthcare professional being a member of a life-long care team for the patient that includes all care teams encountered by the patient at any time, the new medical information corresponding to a new care team event for the patient, pushing, in real time or near real time, the medical information to at least one server that is coupled to the datastore, and causing a second healthcare professional that is not a member of the new care team to be automatically invited to be a member of the new care team. The second healthcare professional may be invited based on analysis of data in the datastore. The data in the datastore may be a life-long health record of the patient. The data in the life-long health record may be analyzed using natural language processing and machine learning to detect patient conditions that need assistance that exceeds core competencies of members of the new care team. The new care team event may be caused by admission of the patient to a facility. Managing healthcare information may also include an artificial conversation entity assisting a healthcare professional to create a summary of a stay of the patient in a medical facility, wherein the summary is based on the life-long health record. Managing healthcare information may also include an artificial conversation entity communicating ongoing information about various stages of a stay of the patient in a medical facility, wherein the ongoing information is based on data in the datastore. The artificial conversation entity may communicate with family members of the patient. Communicating may use email and/or instant messaging. The artificial conversation entity may communicate with family members of the patient to pick up the patient. The artificial conversation entity may communicate with family members of the patient to pick up prescription drugs for the patient.

According further to the system described herein, a non-transitory computer-readable medium contains software that manages healthcare information. The software includes executable code that interacts with a first healthcare professional to allow the first healthcare professional to subscribe to a subset of medical information for a patient in a healthcare information framework having a datastore containing electronic health records for the patient, the first healthcare professional being a member of a life-long care team for the patient that includes all care teams encountered by the patient at any time. The software also includes executable code that interacts with a second healthcare professional to allow the second healthcare professional to post medical information about the patient in the healthcare information framework, executable code that pushes, in real time or near real time, the medical information to at least one server that is coupled to the datastore, and executable code on the at least one server that causes the first healthcare professional to automatically receive the subset of the medical information based on the first healthcare professional subscribing to the subset of the medical information. The first healthcare professional subscribing to the subset of medical information may be subject to authorization and appropriate credentials. The electronic health records provided in the datastore may be life-long electronic health records. Subscriptions to the subset of medical information may be filtered based on time period, patient ID, event type, and/or specific parameters or thresholds of data associated with subscribed events. The software may also include executable code that causes a realtime or near realtime event bus to receive an event in response to the subset of medical information being posted by the second healthcare professional, where the event bus interacts with the server to cause the first healthcare professional to automatically receive the subset of the medical information. The subset of medical information may correspond to a data change event. The data change event may correspond to arrival of results of a diagnostic laboratory test. The subset of medical information may correspond to a new care team event. The new care team event may be caused by admission of the patient to a healthcare facility. The subset of medical information may correspond to a medical appointment event.

According further to the system described herein, a non-transitory computer readable medium contains software that manages healthcare information. The software includes executable code that interacts with a first healthcare professional to allow the first healthcare professional to post new medical information for a patient in a healthcare information framework having a datastore containing electronic health records for the patient, the first healthcare professional being a member of a life-long care team for the patient that includes all care teams encountered by the patient at any time, the new medical information corresponding to a new care team event for the patient. The software also includes executable code that pushes, in real time or near real time, the medical information to at least one server that is coupled to the datastore, and executable code that causes a second healthcare professional that is not a member of the new care team to be automatically invited to be a member of the new care team. The second healthcare professional may be invited based on analysis of data in the datastore. The data in the datastore may be a life-long health record of the patient. The data in the life-long health record may be analyzed using natural language processing and machine learning to detect patient conditions that need assistance that exceeds core competencies of members of the new care team. The new care team event may be caused by admission of the patient to a facility. The software may also include executable code corresponding to an artificial conversation entity that assists a healthcare professional to create a summary of a stay of the patient in a medical facility, where the summary is based on the life-long health record. The software may also include executable code that corresponds to an artificial conversation entity that communicates ongoing information about various stages of a stay of the patient in a medical facility, where the ongoing information is based on data in the datastore. The artificial conversation entity may communicate with family members of the patient. Communicating may use email and/or instant messaging. The artificial conversation entity may communicate with family members of the patient to pick up the patient. The artificial conversation entity may communicate with family members of the patient to pick up prescription drugs for the patient.

The proposed system offers a patient-centric Healthcare Information Framework (HIF) based on a Life-Long Care Team (LCT) and a Life-Long Healthcare Record (LHR) created and maintained for each patient and accessible by the patient and healthcare professionals. The HIF framework includes data store(s) and schemas, authorization and authentication tools, APIs with a distributed event bus, a user experience (UX) layer for mobile and desktop applications, a technology stack with machine learning, artificial intelligence and other components, a HIPAA certified foundation, and a set of runtime services for deployment. The LCT accumulates all care teams encountered by a patient at any time, stratified by healthcare perimeters, such as the Family perimeter, the PCP (Primary Care Physician) perimeter, the Outpatient Care, the Inpatient Care and the Long-Term Care perimeters. The LHR is an accumulated set of all healthcare records captured through patient's life, as used and augmented by each LCT team, including the patient. Furthermore, the proposed system offers custom data views for various members of care teams; event generation and processing mechanisms within the HIF+LCT+LHR triad; subscription by care team members to LHR event and data streams for particular patients providing a continuous delivery of necessary information; added workflow intelligence based on Natural Language Processing of LHR and Machine Learning/Artificial Intelligence subsystem; and enhanced communications between various care teams (with patient and patient's family) using multiple venues and including usage of Artificial Conversational Entities (ACEs) for communications and clinical work.

The HIF may include the following components:
- A set of high-speed, structured & unstructured data store(s).
- A Schema Repository for data structures and other declarative data.
- A fine grained authorization subsystem, allowing per data category, per document and per field credentials for multiple actors.
- A robust set of APIs for own and third-party innovative clinical applications, including a distributed event bus and a UX layer with user interface framework for mobile and desktop applications, including speech and augmented reality.
- Machine Learning, Artificial Intelligence, speech and handwriting recognition technology stack for runtime and batch analytics.
- A HIPAA certified foundation for system deployment.
- A set of runtime services to enable cloud or on premise deployment of the HIF.
- An LCT that may include all care teams a patient has encountered to date and will encounter in the future, each care team utilizing patient's prior healthcare data from the LHR and contributing new data to the LHR. For many US patients, care teams may be stratified into five or more perimeters reflecting different roles of healthcare organizations in the patient care, as follows:
  - The Family perimeter, including patient and patient's family members. A very healthy individual may stay within the Family perimeter for most of his or her life, using OTC drugs and periodic vaccinations and taking certain non-prescribed tests to make sure, for example, that there are no major genetic risks. A patient's family may help, from time to time, with simple therapeutic procedures.
  - The PCP perimeter, including an office of the PCP, laboratory and diagnostics facilities immediately referred by the PCP prior to care escalation, pharmacies providing PCP prescribed drugs, vaccination services, etc. Under PCP supervision, the patient takes periodic prescribed tests, such as a blood test, a treadmill test, a routine X-ray exam, undergoes additional vaccinations (such as a tetanus shot in case of a wound) and may take prescribed medications, for example, for cholesterol or blood pressure control. The role of the PCP is central for the initial compilation of patient's LHR, because the PCP serves as a major source of references to specialists, clinicians and hospitals, is reflected in most admission documents for any care team and receives copies of all laboratory, diagnostics and discharge reports, serving as a key hub of LHR data.
  - The Outpatient Care perimeter includes care teams with specialists, clinicians and other personnel in various care centers, including clinics, ER and physical therapy facilities, associated diagnostic facilities, etc., providing same-day care to patients. Many types of periodic procedures and complex tests, such as colonoscopy or cardiology tests, are done within this care perimeter.
  - The Inpatient Care perimeter includes care teams of surgeons and other clinicians, such as registered nurses and nurse anesthetists located in hospitals, and includes diagnostics and laboratory facilities of the care teams and includes other premises where patient stay overnight. Care teams in this perimeter use and produce an extensive amount of healthcare information and significantly contribute to the EHR.
  - The Long-Term Care perimeter includes care teams in Assisted Living Facilities, Skilled Nursing Facilities, hospices and other providers who offer long-term care to patients with chronic, terminal diseases or post-operative conditions that require lengthy rehabilitation.

Accumulation and maintenance of the LHR and the LCT may evolve as follows:
1. Multiple deployments of the HIF enable a uniform management and intelligent handling of healthcare information in the system.
2. Individual patients register with the system, provide necessary personal information and obtain unified identifiers for constructing LHRs and login credentials for access to healthcare data of the patients.
3. For each patient, the first instance of LCT and LHR is created, which may include (i) indexing and searching for user records within data stores of deployed instances of the HIF; (ii) connecting to external data sources like an EHR of a PCP, other EHRs where HIF has not yet been deployed, HIEs, etc., for obtaining a more complete list of care teams and available healthcare records; (iii) inquiring additional healthcare data from patients; (iv) connecting wearable health monitors of the patient and other sources of patient-generated healthcare information with the HIF; (v) organizing healthcare information from all such sources, such as prioritizing most recent information, most authoritative information, etc.
4. Providing EHR on-demand to new and existing care teams. Adding new care teams to an appropriate LCT perimeter and modifying existing care teams according to detected changes. Offering each LCT member subscriptions to EHR information on patients filtered by a variety of parameters and instantly available subject to system events, such as arrival of new data, patient admission, release or appointment in a care facility, etc. Such real-time data access capability is part of what distinguishes the system described herein from current state of the art, which often relies on manual coordination of care or uses older batch modes for shipping healthcare data between siloed applications.
5. Creating new instances of LCT and LHR. This phase includes obtaining new patient-related healthcare information from various sources – provided by new care teams, generated by additional deployments of HIF, by follow-up information from previous care teams, by users via wearable health monitors, etc. This corresponds to different types of events generated by the system (for example, a data change event, a new care team event, a follow-up event, a physician appointment event, a hospital discharge event, etc.), flowing within the distributed events bus of the HIF and accessed by various care teams, including possibly the patient herself.

The LHR-LTC-HIF triad may enable several advantages for the healthcare stakeholders. The following high-level descriptions provide some examples of this.

Each deployment may provide custom on-demand views of an LHR of each patient to different care teams/members by joining fragments of data according to filtering and other rules. For example, a PCP (Primary Care Physician) may create views that include dynamics of blood cholesterol, sugar and vitamins D and B12 levels for a particular patient, while excluding sugar level and adding X-ray tests for a different patient.

An always-up-to-date data access for LCT members (care teams and particular healthcare professionals) may be based on publishing and subscribing to HIF services, which, in turn, may utilize an event-based data acquisition and distribution approach as described in the following:

Defining different event types/levels, such as a data change event (for example, a new device reading, a new lab or surgery report entered into a HIF data store, etc.), an addition of a new care team to an LCT of a patient, admission and discharge events and patient visits for various care teams and LCT perimeters, changes in patient location, scheduling a medical appointment, etc.

New events within an HIF deployment may form an event stream published into an HIF realtime or near realtime event bus for consumption by LCT members. Each LCT member (team or individual) may subscribe, subject to authorization and appropriate credentials, to a portion of an event stream within the HIF event bus for a particular patient or multiple patients. For example, one care team may subscribe to all lab test reports for a patient A and all physical therapy updates for a patient B, while another care team may subscribe to all CT scan images for a patient C. Subscriptions may include time period, patient IDs, event types, specific parameters or thresholds of data associated with subscribed events, etc. Such subscriptions guarantee that appropriate data will be instantly delivered to care teams, creating high levels of awareness about condition of a patient and potential problems.

Advanced AI-based processing of an LHR of a patient may add significant workflow intelligence and modify care processes. For example, an NLP (Natural Language Processing) combined with continuously trained Machine Learning (in particular, Neural Network) based rules may indicate a need to call in an additional specialist from a previous care team or with a particular expertise when necessary, provided that an area expertise of an additional specialist exceeds or complements core competencies of members of the new care team. This may include, for example, auto-including an on-call psychiatrist if sexual-abuse is documented in the LHR. Other applications of intelligent processing of the LHR in combination with LCT may include:

Intelligent escalation of a patient emergency (if MD is not available).

Intelligent follow-up on a referral made but not acted upon.

Intelligent patient outreach (e.g. sending communication to diabetics missing HbA1c, not contacting deceased patients, etc.)

The HIF-LCT-LHR triad enables various mechanisms of communication and coordination within and between care teams. Communications may be event and workflow intelligence driven and may include the following:

Traditional encrypted email / text communications.

Shared data viewing and/or editing in the publishing and subscription event-based model explained elsewhere herein.

Dedicated channels between care teams or within a care team, similar to Slack or other contemporary workplace communications tools.

Communications facilitated and driven by Artificial Conversation Utilities (ACEs, chatbots). For example, after a patient is admitted into a hospital or other inpatient care facility, an ACE may analyze reports for each phase of treatment of a patient and choose a communication modality (such as email or texting) for updating a family of the patient on the progress. Additionally, another or the same ACE may assist a physician in writing a treatment summary before discharge of a patient.

BRIEF DESCRIPTION OF THE DRAWINGS

Embodiments of the system described herein will now be explained in more detail in accordance with the figures of the drawings, which are briefly described as follows.

DETAILED DESCRIPTION OF VARIOUS EMBODIMENTS

The system described herein offers mechanisms for building a patient-centric Healthcare Information Framework (HIF) based on a Life-Long Care Team (LCT) and a Life-Long Healthcare Record (LHR) created and maintained for each patient and accessible by patients and healthcare professionals, provides event generation and processing mechanisms and subscriptions by care team members to LHR event and data streams ensuring a continuous delivery of necessary information, enables workflow intelligence based on Natural Language Processing and Machine Learning/Artificial Intelligence subsystem, and enhances communications between various care teams through the use of Artificial Conversational Entities (ACEs) for communications and clinical work.

Figure 1:
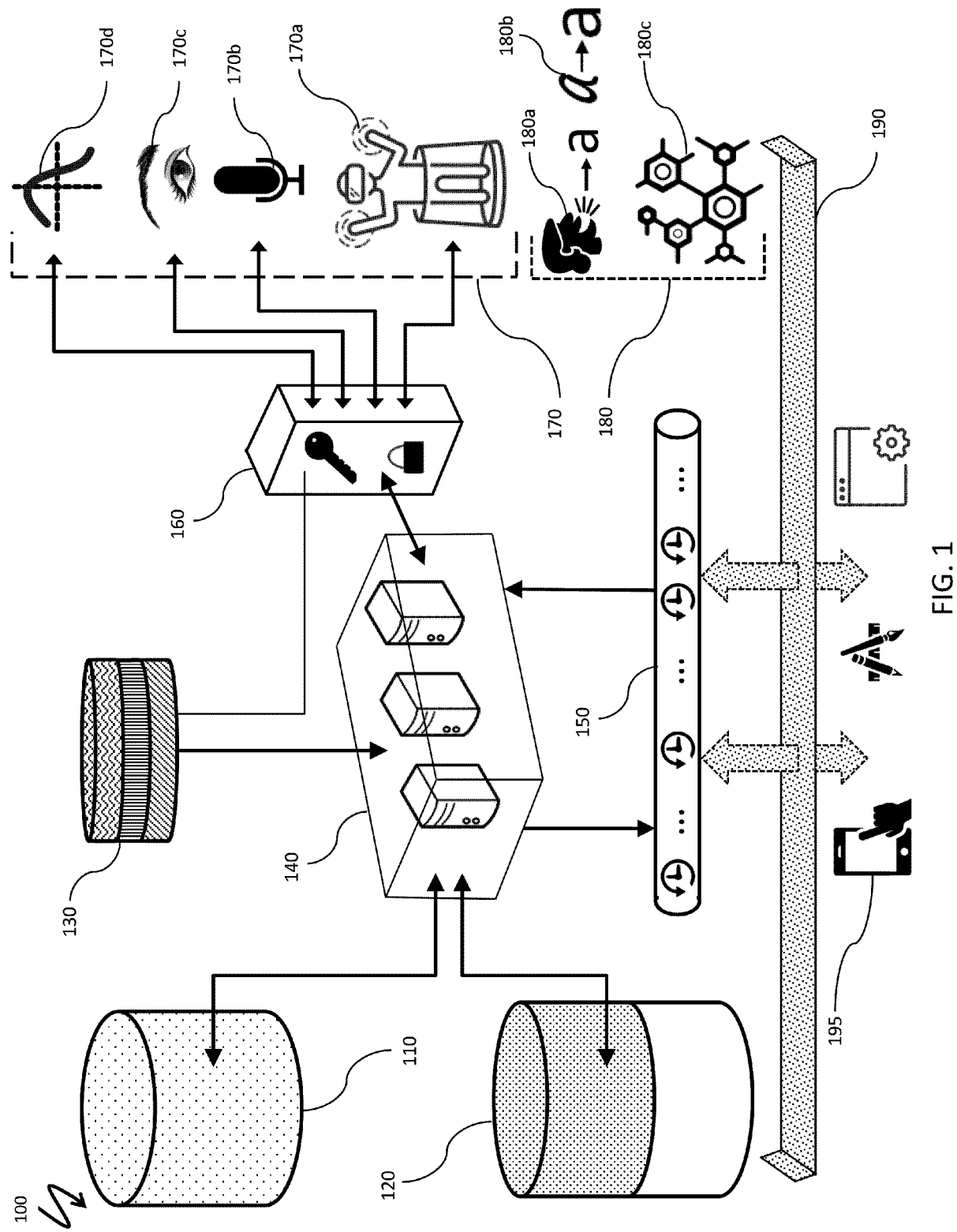
FIG. 1 is a schematic illustration of the HIF architecture and components, according to an embodiment of the system described herein.

FIG. 1 is a schematic illustration 100 of HIF architecture and components. EHR data from an existing data store 110 with legacy healthcare information is pre-existing at the time of deployment of a HIF-based system. Data from the data store 110 may be retrieved into the system, deciphered, converted where necessary into new data formats and placed into a new data store 120, which is also storing newly arriving EHR data. Data deciphering, conversion and storage is enabled by a schema repository 130, which contains descriptions of and relations between all database record formats for legacy and new data. One or more servers 140 includes data logic and API support component that retrieve, process and convert data and process external events arriving into the system through a distributed event bus 150. The one or more servers 140 also handle internal events placed into an event bus 150 by the system software, interpret data schemes from the schema repository 130 and interacts with other components of the system as explained in more detail elsewhere herein. The server(s) 140 may also provide a bidirectional access to legacy healthcare systems and modify healthcare information in the legacy systems by, for example, modifying data in the existing datastore 110 using healthcare information processed by the HIF.

External events may arrive into the system driven by user needs (patients, physicians, insurers, healthcare facilities and other healthcare players) through various venues, including third party healthcare applications 195 enabled by the HIF and interacting with the system through a HIPAA compliant deployment framework 190. Note that data processed by software applications of the system or by a third party may be provided in a format that is dynamically adapted by the system to each software application.

External events may include data change events, data requests by care teams, medical appointments for doctor visits, scheduled procedures and other types of treatments, drug prescriptions and drug refill confirmations and orders, admissions to and releases from medical facilities, medical reports, recommendations and alerts of different types, requests for interaction and scheduled interactions between different members of the LCT, patient monitoring info, warnings and regular notifications and data submissions from wearable devices in patient's possession, etc.

Internal events may be placed into the distributed event bus 150 by various system software modules running within the server(s) 140. The internal events may be caused by the functioning of data logic, for example: finding inconsistencies between EHR records from different healthcare facilities at the data entry and/or retrieve phase and directing requests for further analysis or corrections of the data to respective vendors or to an analytics system; reacting to medical appointments, patient admissions and releases and other similar events by automatically collecting relevant patient data from data stores and directing patients to appropriate healthcare facilities; processing billing and insurance requests following medical appointments, drug prescriptions, hospital stays, etc.

The system may provide various visual, sensor, audio and analytic access methods to the stored data, enabling various data mining, control, processing, presentation and other applications for healthcare professionals, patients and other parties. Due to high sensitivity of healthcare data, all interactions between the server(s) 140 and various data access mechanisms may only be provided via an authorization subsystem 160, such as an AAA (authorization, authentication and audit) server. Mechanisms for data access protected by an authorization system 160 may be represented as a UX layer 170 and may include, without limitation, a set of AR-based (with Augmented Reality capabilities), touch and motion enabled UX mechanisms 170a, audio input mechanisms 170b, visualization mechanisms 170c, and analytics/data presentation mechanisms 170d.

The system may also include a technology stack 180 for facilitating data input and AI applications with technologies such as voice recognition 180a, handwriting recognition 180b and machine learning 180c based on neural networks or other mechanisms.

Figure 2:
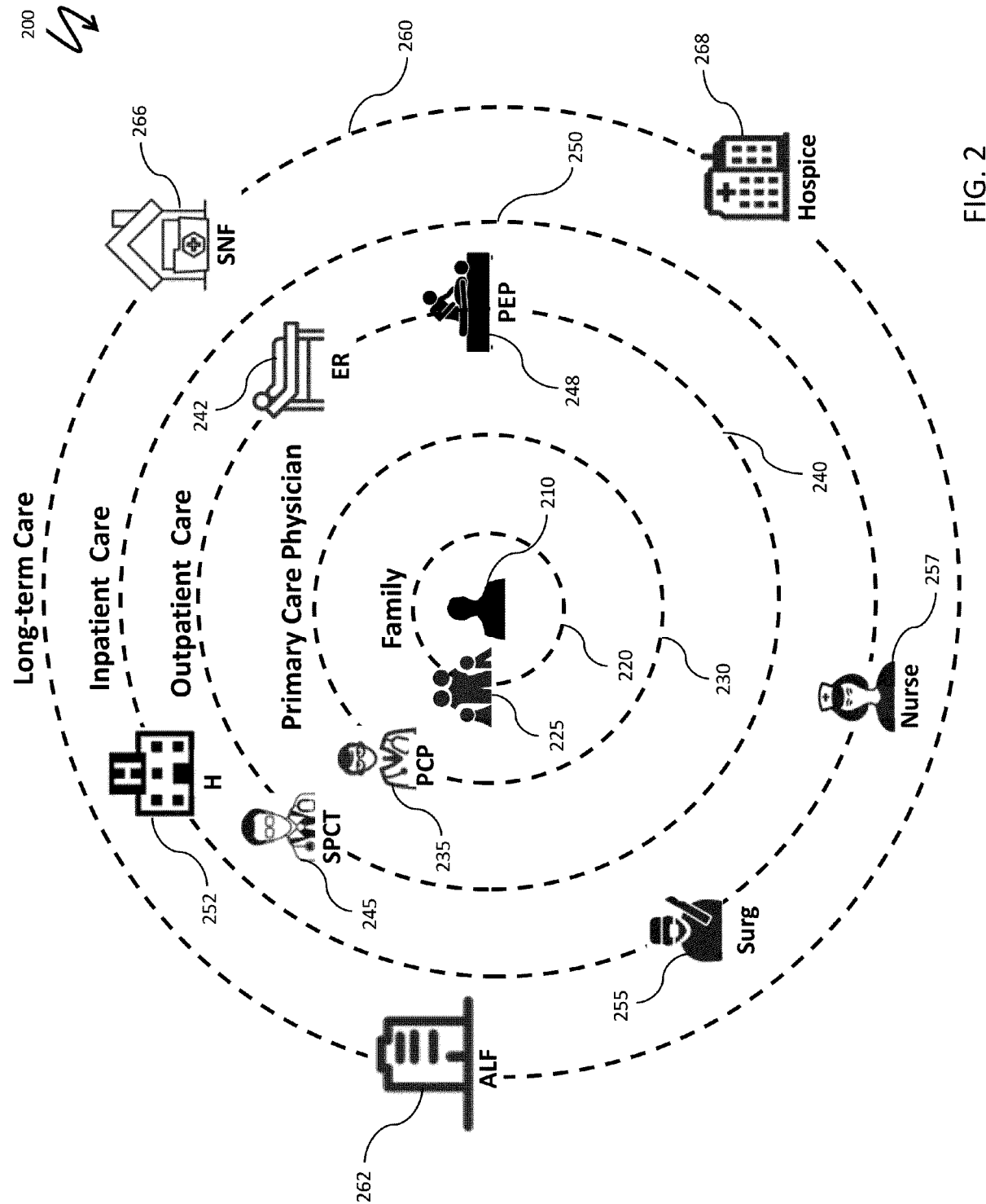
FIG. 2 is a schematic illustration of a general layout of LCT perimeters, according to an embodiment of the system described herein.

FIG. 2 is a schematic illustration 200 of a general layout of LCT perimeters (details on each LCT perimeter are discussed in more detail elsewhere herein). The perimeters, or layers of healthcare history and interactions with the healthcare system of a patient, enable build-up of a complete and uninterrupted LHR and improve care quality and efficiency by applying data logic to identify efficient treatment strategies, as well as risks and conflicts in the care process.

FIG. 2 shows five LCT perimeters for a patient 210:
1. A Family perimeter 220 where healthcare needs of the patient 210 may be supported by a family 225 of the patient 210.
2. A Primary Care Physician (PCP) perimeter 230, where a leading care provider is a PCP 235 of the patient (and a staff of the PCP 235, not shown in FIG. 2).
3. An Outpatient Care perimeter 240, where the patient 210 encounters specialists (doctors) 245 and may stay for short periods of time (not overnight) in different types of facilities, including an ER 242 and a physical therapy cabinet or facility (PEP) 248.
4. An Inpatient Care perimeter 250, where a characteristic care facility is a hospital 252 and care provider individuals may include a surgeon (Surg) 255 and a nurse 257.
5. A Long-Term Care perimeter 260 with Assisted Living Facilities (ALF) 262, Skilled Nursing Facilities (SNF) 266 and Hospices 268 providing a (non-exclusive) list of alternatives for prolonged care.

Figure 3:
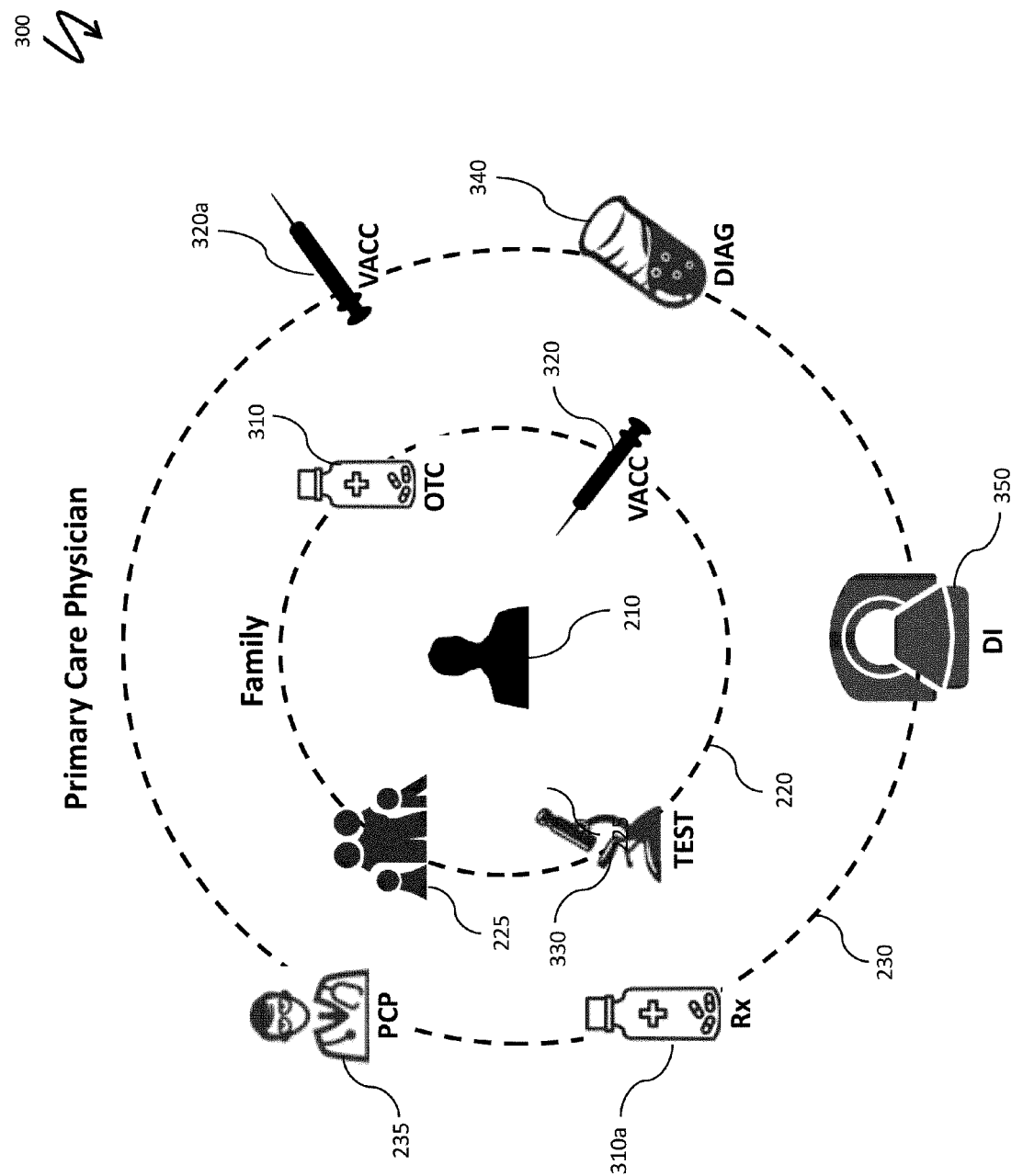
FIG. 3 is a schematic illustration of Family and PCP LCT perimeters, according to an embodiment of the system described herein.

FIG. 3 is a schematic illustration 300 of two LCT perimeters for the patient 210: the Family perimeter 220 and the PCP perimeter 230, with details on each of the perimeters 220, 230. Patient care options for the Family perimeter 220 may include taking Over-the-Counter (OTC) drugs 310, voluntary vaccinations (VACC) 320, such as a flu vaccination or a pneumonia vaccination for senior patients, offered by pharmacies, and various (non-prescribed) tests, such as blood pressure monitoring at a local pharmacy, but also including genetic tests.

Unlike conventional healthcare practices where the family perimeter does not produce reliable EHRs, the proposed system supplies patients with tools and applications to record every health-relevant event and encounter with the healthcare system, including non-prescribed OTC drugs, vaccinations and tests that become part of the LHR and are stored in the system, as explained elsewhere herein (see, for example, the item 120 in FIG. 1 and FIG. 2). Subsequently, system analytics and data logic may build important health characteristics of the patient 210, such as BP (blood pressure) profile and genetic rest results. The health characteristics may be accessible by care professionals from other LCT perimeters and/or automatically used by the system to assess benefits and risks of future treatment methods and to improve reliability of diagnostics.

Patient care options for the PCP perimeter 230 may include taking prescribed drugs (Rx) 310a, receiving prescribed vaccinations (VACC) 320a, for example, a preventive tetanus shot, laboratory diagnostic tests (DIAG) 340, and digital imaging tests (DI) 350, such as an MRT.

Viewed jointly with the portion of LHR reflecting the Family perimeter 220, procedures and care methods offered by the PCP may be more beneficial for a patient compared with conventional approaches. For example, knowing a BP profile of a patient built at the Family perimeter 220 may help better understand patient risks during a PCP office visit and a point BP measurement by PCP staff. Analogously, information about a recent voluntary patient vaccination may alter or delay a PCP decision about prescribing a new vaccination, while information about genetic test results of a patient may direct a PCP to different instructions for diagnostic blood testing. Such advanced care may not solely rely on qualifications and experience of a PCP but may be recommended by the system in an assisting mode, using, for example, a chatbot-based conversation with the PCP.

Figure 4:
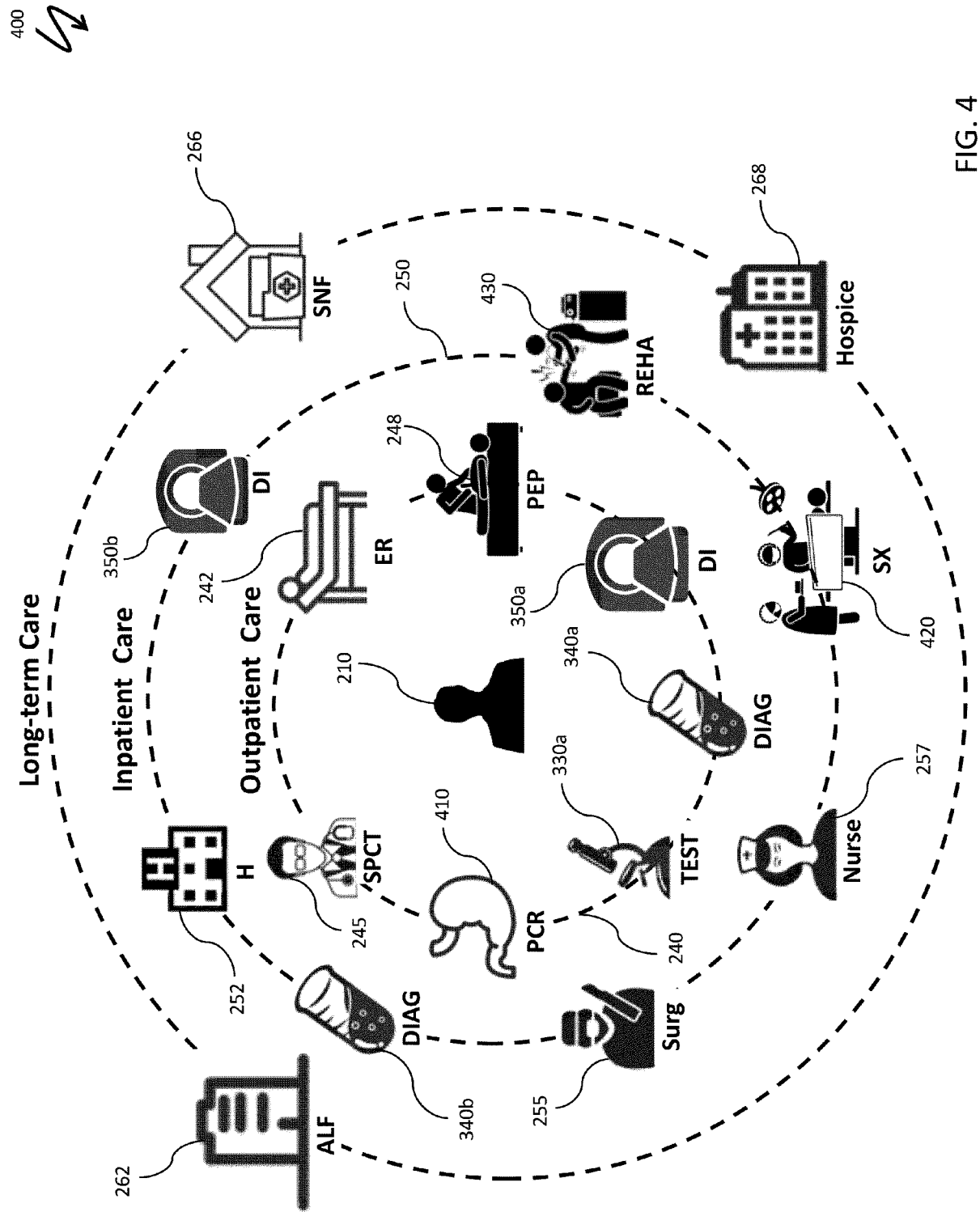
FIG. 4 is a schematic illustration of Outpatient Care, Inpatient Care and Long-Term Care LCT perimeters, according to an embodiment of the system described herein.

FIG. 4 is a schematic illustration 400 of three more LCT perimeters for the patient 210, introduced, in particular, in FIG. 3: the Outpatient Care perimeter 240, the Inpatient Care perimeter 250, and the Long-Term Care perimeter 260, with details on each of the perimeters 240, 250, 260.

Patient care options for the Outpatient Care perimeter 240, in addition to the ER stay 242 and the physical therapy facility 248, explained elsewhere herein (see, in particular, FIG. 2), may include various medical tests 330a, laboratory diagnostics 340a and digital imaging tests 350a, also explained in conjunction with the Family perimeter 220 and the PCP perimeter 230 in FIG. 3. Additionally, the perimeter 240 may include various outpatient procedures (PCR) 410, such as colonoscopy, kidney stone treatment, lumbar epidural steroid injection, etc. Medical tests and procedures in the Outpatient Care perimeter 240 may be directed by specialists 245 (introduced in FIG. 2).

Analogously, care options for the Inpatient Care perimeter 250 may include laboratory diagnostics 340b and digital imaging tests 350b characteristic for a patient stay in the hospital 252. In many cases, such a patient stay in a hospital may include a surgery (SX) 420, conducted by a surgeon 255, assisted by nurse(s) 257 and other medical staff. A post-surgery rehabilitation (REHA) 430 may be another treatment option for the Inpatient Care perimeter.

The content of the outer Long-Term Care perimeter 260 has been explained elsewhere herein (see FIG. 2 and the accompanying text) and contains the same care facilities 262, 266, 268.

The same consideration of constant informational and other types of interaction between various LCT perimeters, facilitated and partially or fully automated by the proposed system, applies to the three perimeters 240, 250, 260 illustrated in FIG. 4. For example, knowledge about patient drug allergies or specifics of previous blood tests recorded at various perimeters and contained in patient's LHR may significantly improve care and reduce complications risks at the Inpatient Care perimeter 250.

Figure 5:
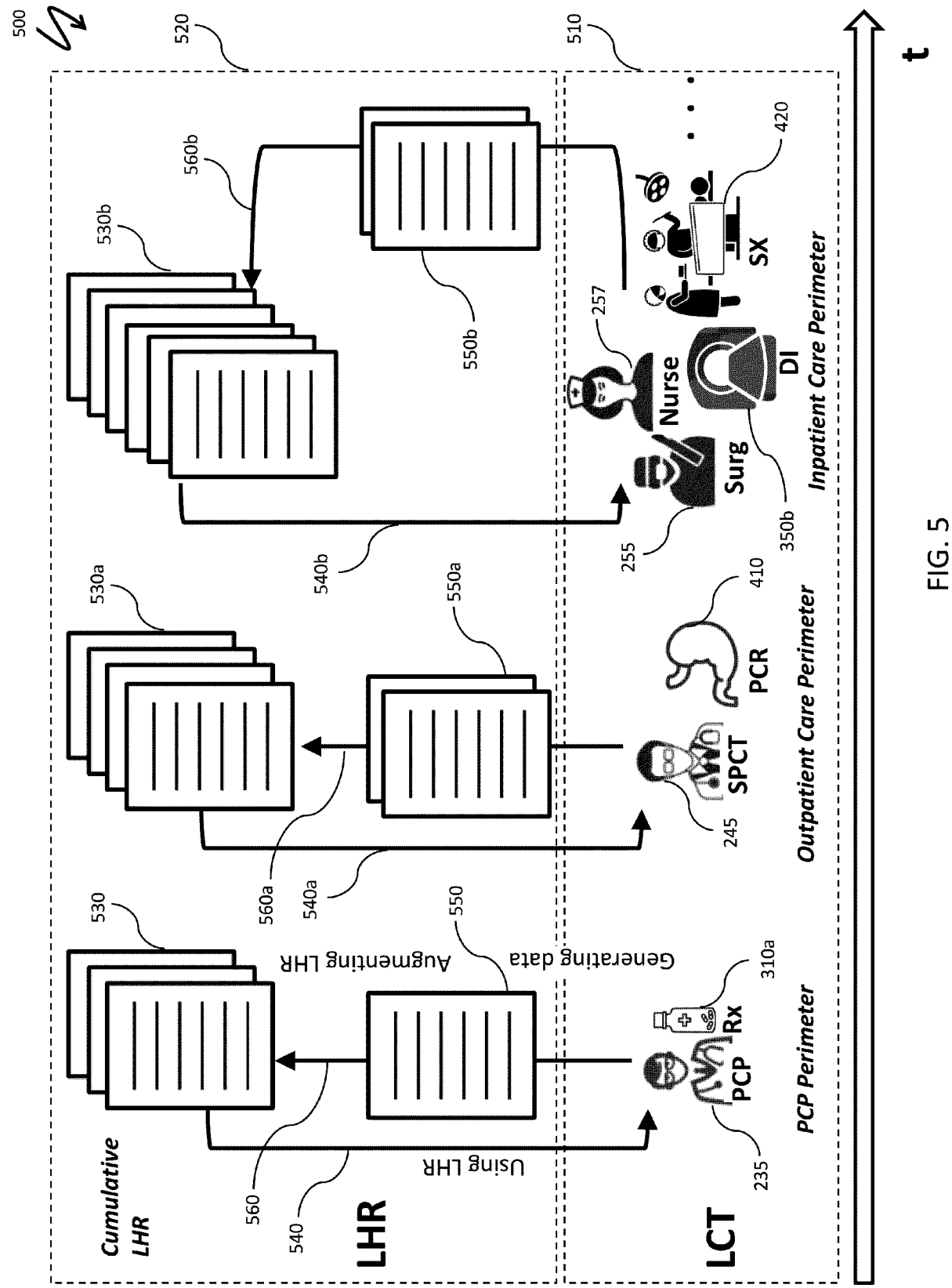
FIG. 5 is a schematic illustration of LHR build-up, according to an embodiment of the system described herein.

FIG. 5 is a schematic illustration 500 of LHR (Life-Long Healthcare Record) build-up. An LCT portion 510 schematically shows a particular history of patient admission at three different LCT perimeters: a PCP perimeter where a PCP 235 prescribes an Rx drug 410a; an Outpatient Care perimeter where a specialist 245 conducts a procedure 410; and an Inpatient Care perimeter, where a surgeon 255, assisted by a nurse 257 first obtain the digital imaging test 350b and then participate in a surgery 430.

An LHR portion 520 schematically illustrates build-up of an LHR of a patient through the encounters by the patient with LCT members and perimeters. A pre-existing instance 530 of the LHR may be used by the PCP 235, as indicated by an arrow 540. Based on studying the existing LHR and studying condition of the patient during an appointment, the PCP 235 decides to prescribe the drug 310a. All information on the appointment, including PCP notes and the Rx, is included in a generated incremental EHR record 550, which augments the LHR, as indicated by an arrow 560. Analogously, an enhanced instance 520 of the LHR may be used by a specialist 245 (an arrow 540a) and an incremental record 550a of a patient admission and conducting a procedure 410 may be added to the LHR (an arrow 560a). In the same way, an LHR instance 530b, an LHR usage (an arrow 540b), and an incremental record 550b from the digital imaging test 350b and the surgery 420 may be used to augment the LHR (an arrow 560b).

Figure 6:
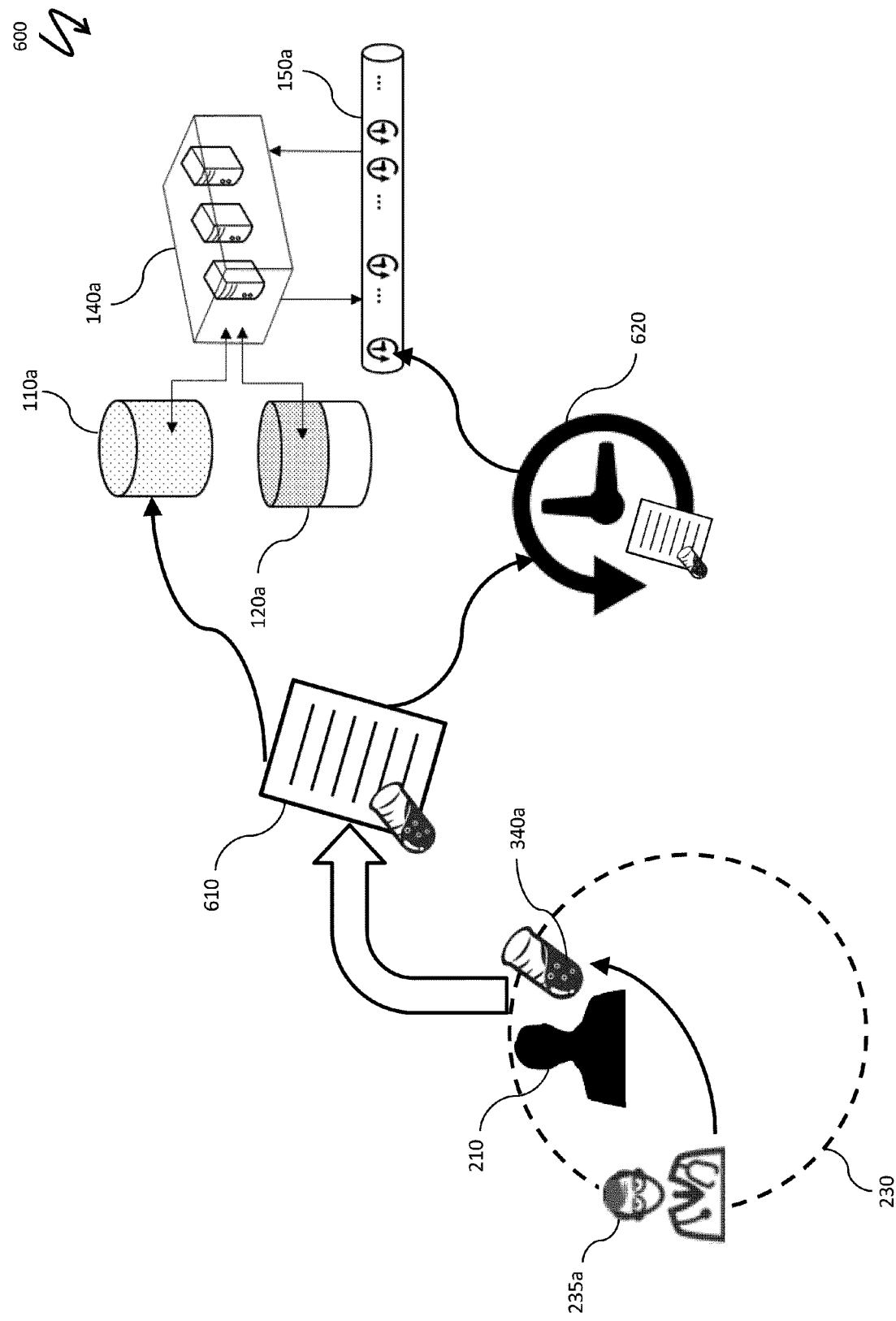
FIG. 6 is a schematic illustration of generating and posting to an HIF a data change event, according to an embodiment of the system described herein.

FIG. 6 is a schematic illustration 600 of generating and posting to an HIF a data change event. A primary care physician 235a orders the laboratory diagnostic test 340a for the patient 210 within the PCP perimeter 230, as explained elsewhere herein (see, for example, FIG. 2, FIG. 3, and the accompanying texts). Upon the arrival of results 610 in text form, the results 610 are entered into the HIF installation, which in FIG. 6 is shown as including an existing data store 110a, a new data store 120a, server(s) 140a, and an event bus 150a. Simultaneously, a new data change event 620 is automatically created by the system and added to a stream of events in the event bus 150a, i.e. published to the event bus, thus signaling an arrival of a new piece of data and availability of the data to LCT members.

Figure 7:
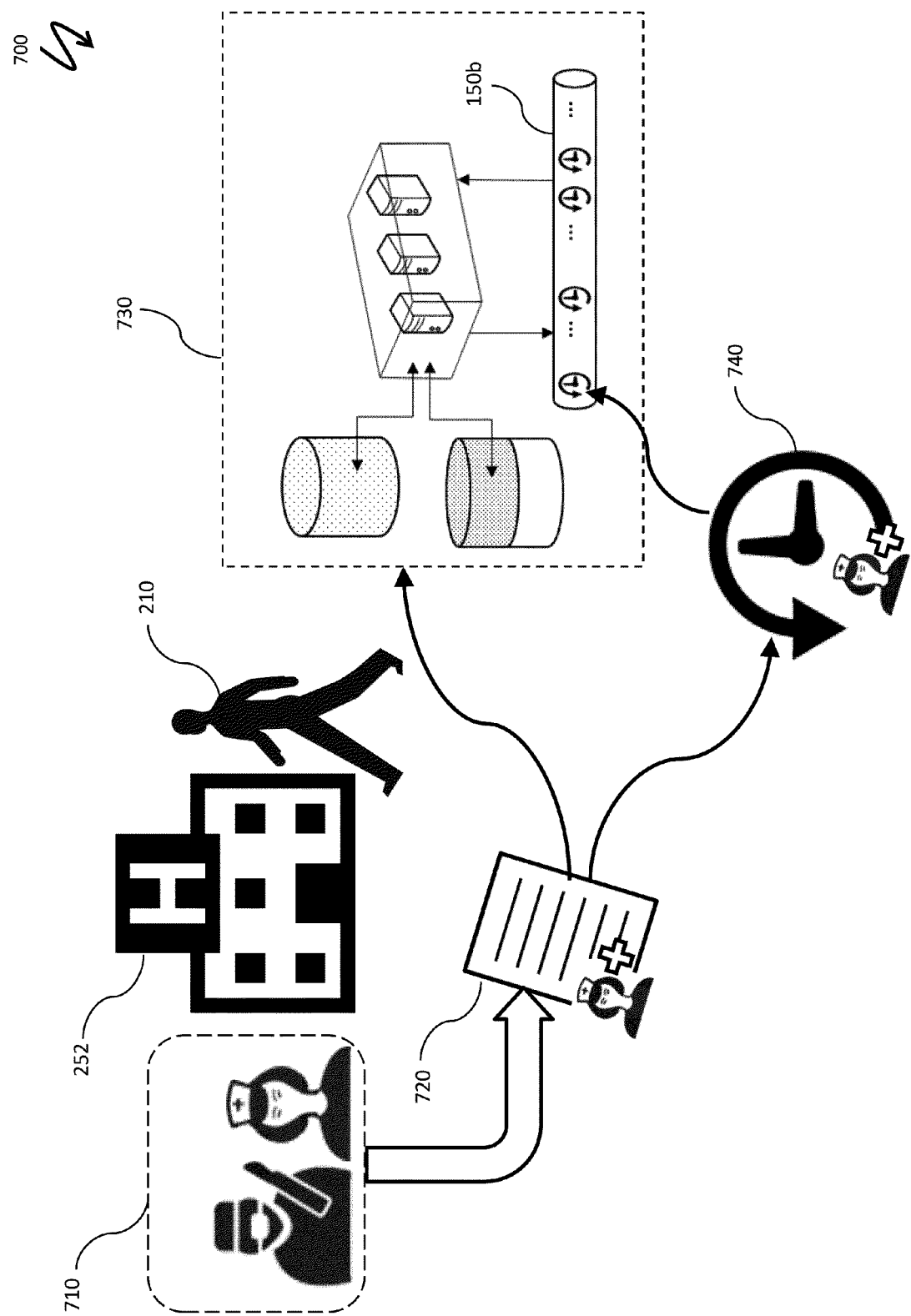
FIG. 7 is a schematic illustration of generating and posting to an HIF a new care team event, according to an embodiment of the system described herein.

FIG. 7 is a schematic illustration 700 of generating and posting to an HIF a new care team event. In the example of FIG. 7, a new care team 710 is assembled following an admission of a patient 210 to the hospital 252, as explained elsewhere herein (see, in particular, FIG. 4 and the accompanying text). Once EHR information 720 (part of the LHR for the patient 210) on the new care team becomes available, the EHR information 720 is stored in an HIF installation 730 (explained in more details in connection with FIG. 1 and FIG. 6). Simultaneously, a new care team event 740 is created and published to the event bus 150, making information about the new care team available to the existing LCT.

Figure 8:
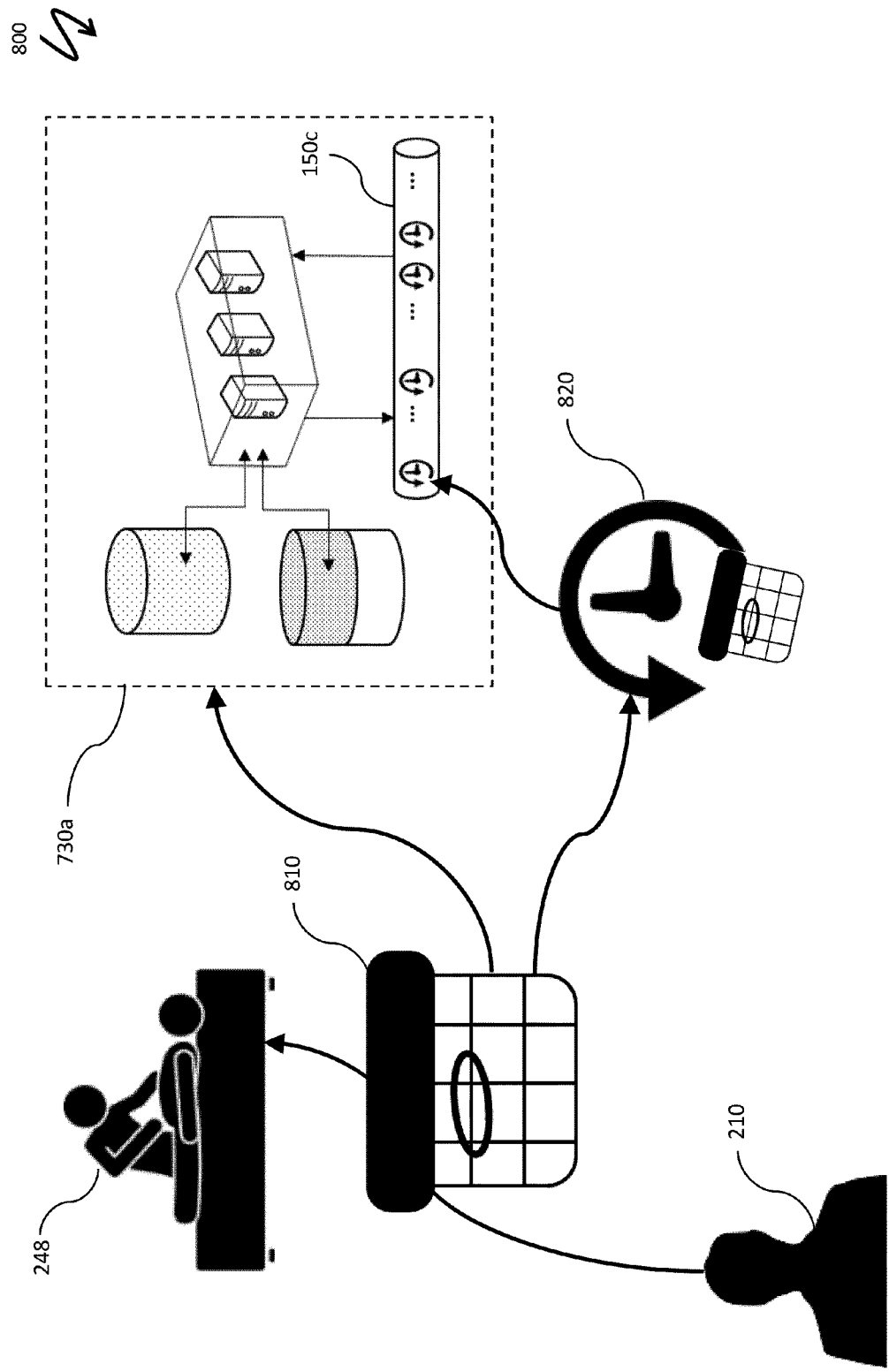
FIG. 8 is a schematic illustration of generating and posting a medical appointment event to an HIF, according to an embodiment of the system described herein.

FIG. 8 is a schematic illustration of generating and posting a medical appointment event to an HIF. An appointment 810 for visiting the physical therapy facility 248 is scheduled for the patient 210 using a scheduling feature of the HIF. Generated EHR information about the appointment is stored in an HIF installation 730a and a simultaneous scheduling event 820 is published to the event bus 150c, making the LCT aware of the scheduled visit.

Figure 9:
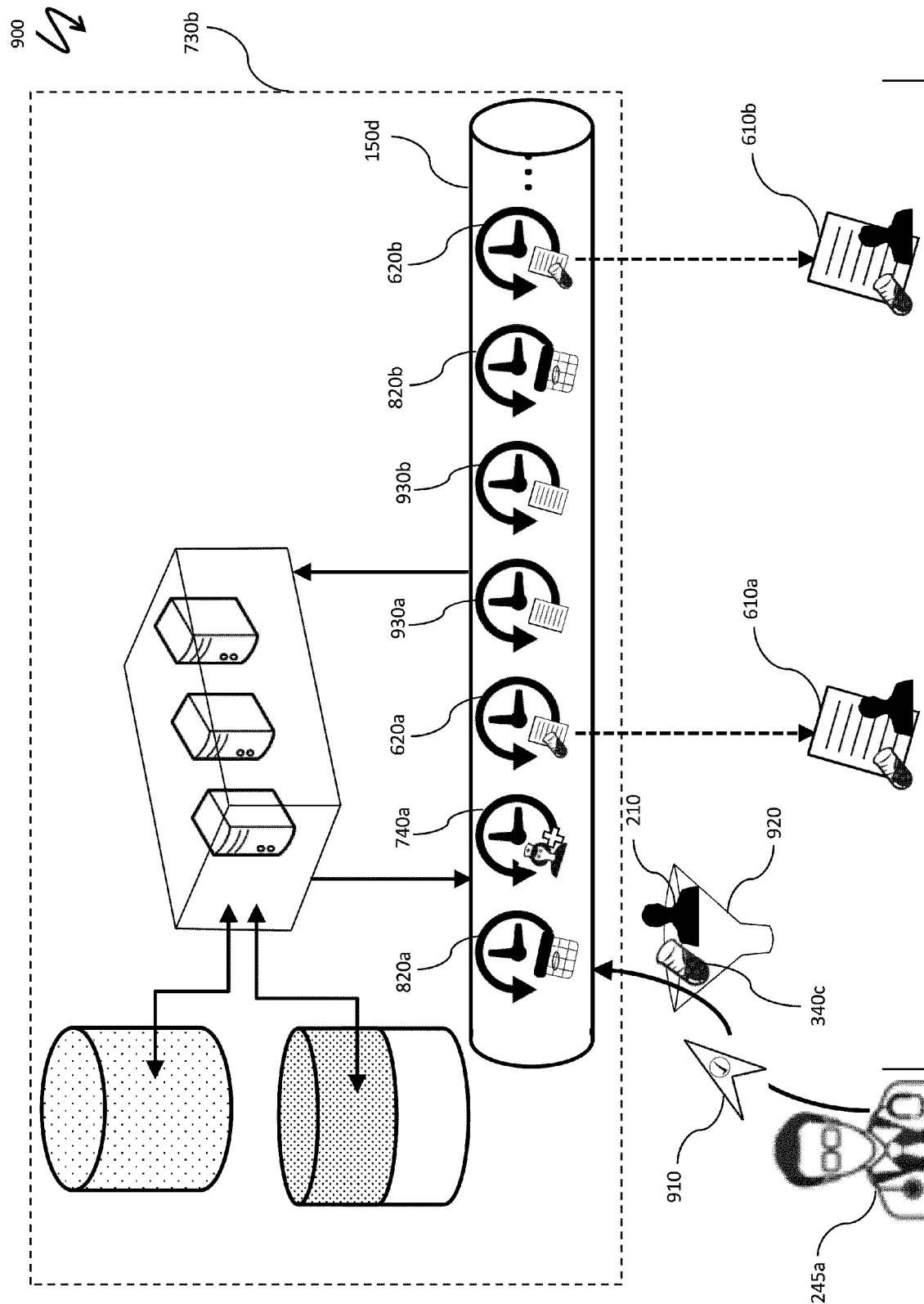
FIG. 9 is a schematic illustration of subscribing to event streams, filtering, and delivering EHR data to healthcare professionals, according to an embodiment of the system described herein.

FIG. 9 is a schematic illustration of subscribing to event streams and filtering and delivering EHR data to healthcare professionals. A realtime or near realtime event bus 150d, part of an HIF installation 730b, carries an event stream, created by various changes in the system, as explained elsewhere herein (see, for example, FIGS. 6-8 in connection with three types of events). A healthcare professional 245a, part of an LCT for the patient 210, may submit a subscription 910 to receive needed patient information when the information first appears as part of an LHR of the patient 210. The member 245a of the LCT may have multiple subscriptions and may define filters 920 to receive specific types of information; in FIG. 9, the healthcare professional 245a requests results of all laboratory diagnostic tests 340c for the patient 210. (Note that a member of the LCT may inquire for more granular test results, e.g. only certain indications of a blood test). Once the subscription and the filter are defined, the event stream in the event bus will be scanned by all such subscriptions, so that irrelevant events (in this case, scheduling events 820a, 820b, new care team event 740a, other events 930a, 930b) will be skipped by the subscription 910 and only appropriate events 620a, 620b will signal the presence of relevant test results. Accordingly, relevant EHR records 610a, 610b will be delivered to the healthcare professional 245a and entered into that LCT member's HIF client application.

Figure 10:
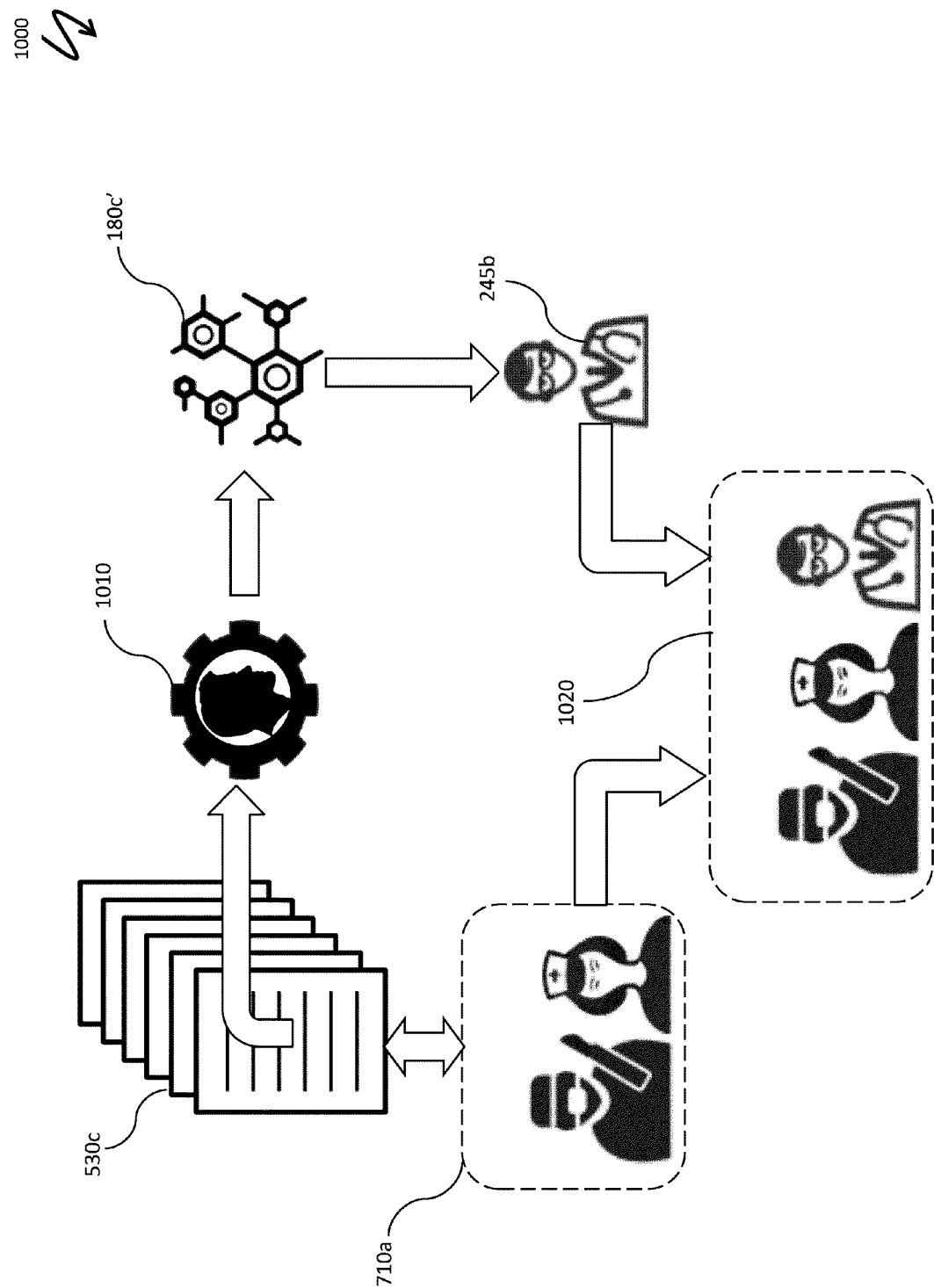
FIG. 10 is a schematic illustration of enhanced workflow level intelligence in the system, according to an embodiment of the system described herein.

FIG. 10 is a schematic illustration of enhanced workflow level intelligence in the system. A new care team 710a (see FIG. 7 for details) has been assembled for a patient and has access to an accumulated EHR history of the patient, that is, an LHR instance 530c. A Natural Language Processing component 1010 of the technology stack that is available in the HIF may analyze the LHR 530c and feed results thereof into a classifier or other AI algorithm built on the basis of the machine learning component 180c'. An outcome of such analysis and classification may be a necessity to invite an additional team member, a healthcare professional 245*b* with specialization in a certain healthcare area needed for a particular cure and missing from qualifications of the care team 710*a*. Subsequently, a expanded care team 1020 may include the specialist 245*b* based on automatic recommendations of the NLP and ML modules.

Figure 11:
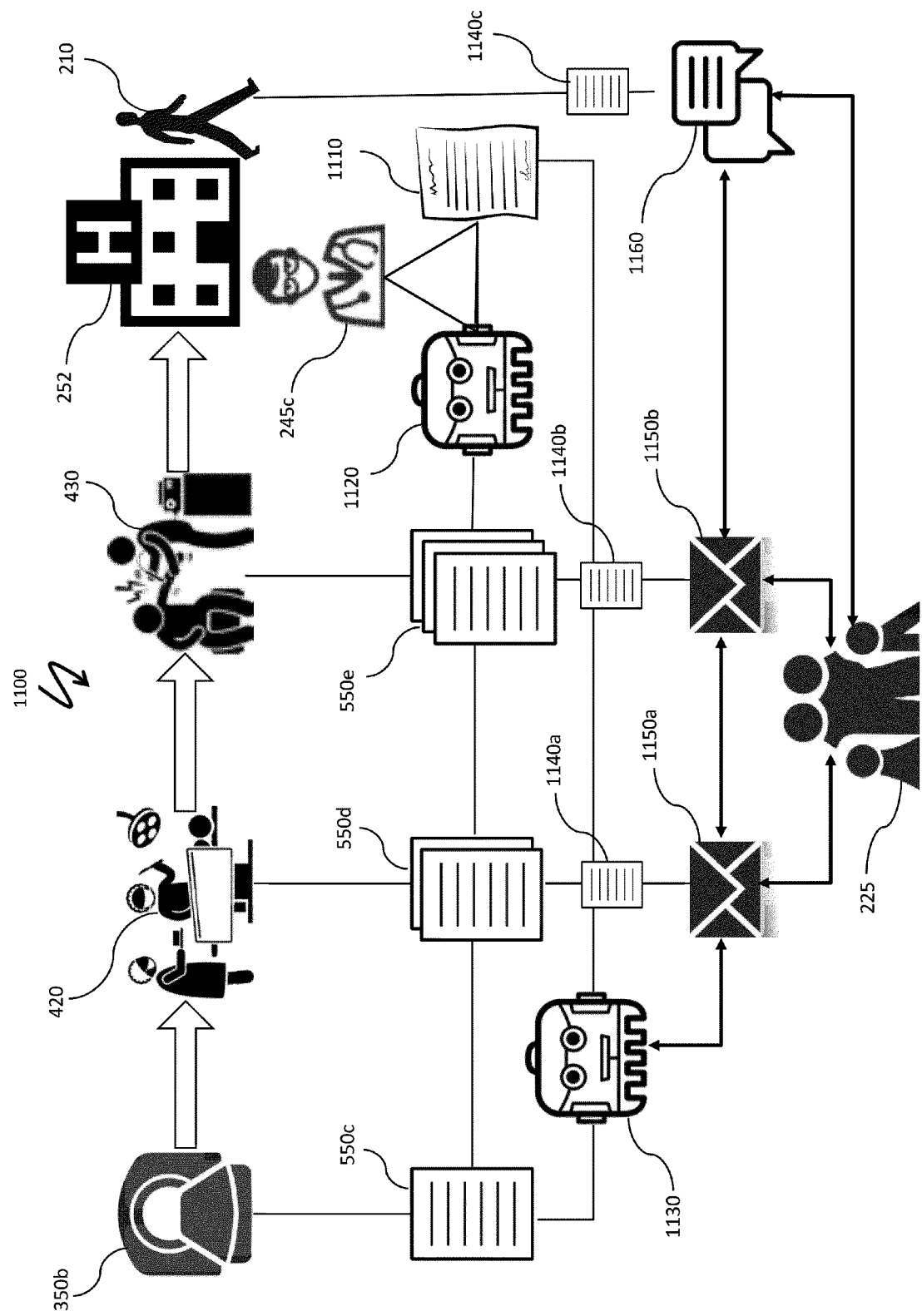
FIG. 11 is a schematic illustration of usage of Artificial Conversational Entities for clinical work and communications, according to an embodiment of the system described herein.

FIG. 11 is a schematic illustration of usage of Artificial Conversational Entities for clinical work and communications. During a stay of the patient 210 in the hospital 252, the patient 210 may undergo several stages of cure, such as the digital imaging test 350*b*, a surgery 420, rehabilitation procedure(s) 430, until finally the patient 210 is discharged from the hospital 252. In parallel, consequential portions of the LHR are recorded and accumulated at each phase, as illustrated by EHR portions 550*c*, 550*d*, 550*e*. At the discharge, a healthcare specialist 245*c* is expected to provide a summary 1110 of patient's stay, cure and condition. An Artificial Conversational Entity (ACE) 1120 may assist the specialist 245*c* in creating the summary 1110, utilizing not only the locally created cumulative EHR record 550*e* but the whole LHR with patient's healthcare history and patient's condition preceding the hospital stay (not shown in FIG. 11).

Additionally, the patient centric HIF installation for the patient 210 may communicate to the family 225 of the patient 210 (and/or to other authorized and interested parties) ongoing information about various stages of a stay of the patient 210 in the hospital. Compilation of such intermediate information and choice of communication venues may be delegated to another ACE 1130. In FIG. 11, the ACE 1130 may compile information snippets 1140*a*, 1140*b*, 1140*c* on the patient's condition, stay and discharge and choose communication venues for delivering the information. Thus, for initial stay periods, the ACE 1130 may choose secure email communications 1150*a*, 1150*b*, while for discharge information 1140*c*, which may include, for example, request for a family member to pick up the patient at the hospital at a certain time or to pick up prescription medicine for the patient (ordered by the hospital or other healthcare facility immediately prior to the patient's discharge), the ACE 1130 may use mobile or other instant messaging 1160.

Figure 12:
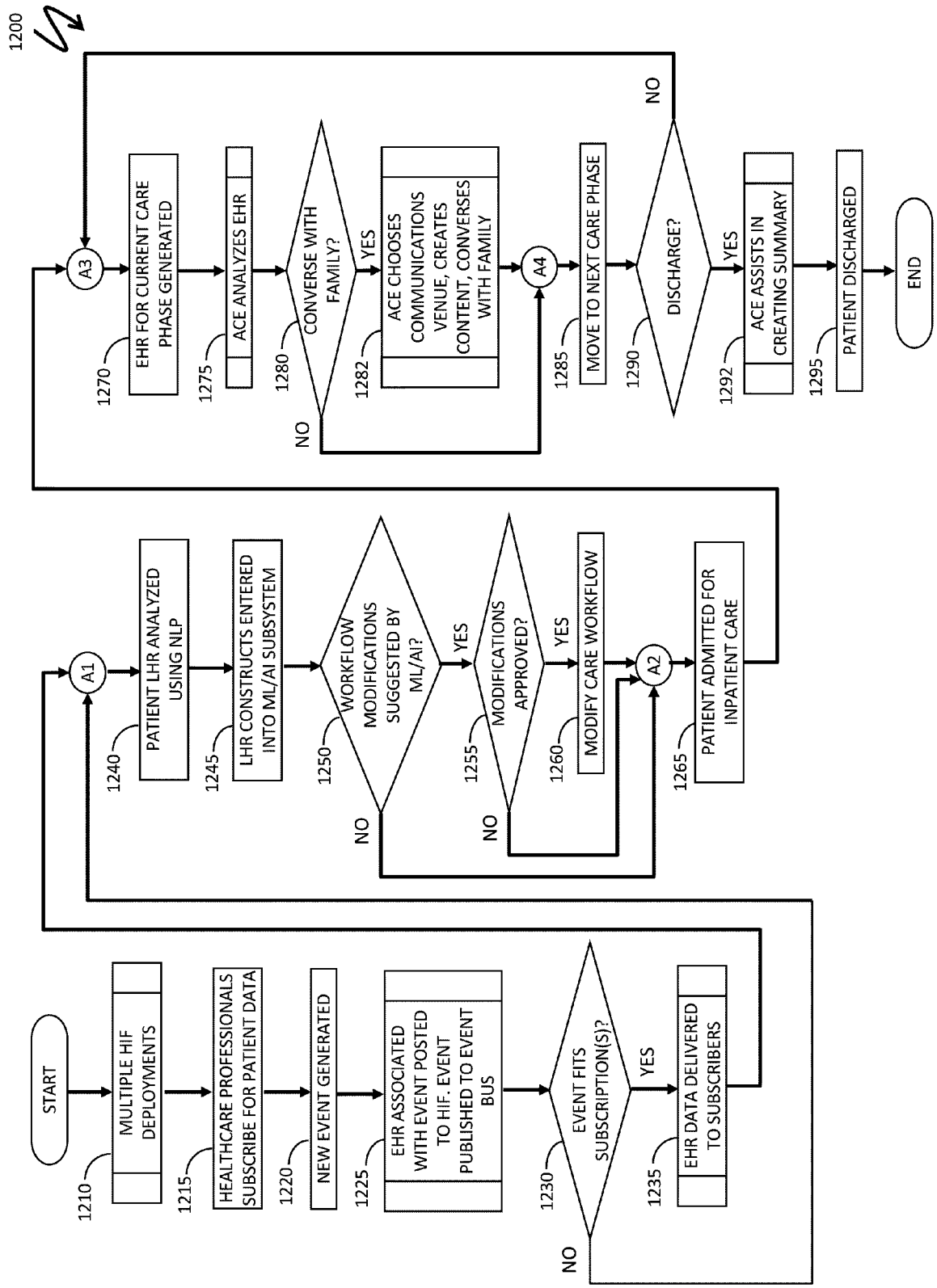
FIG. 12 is a system flow diagram illustrating system functioning in connection with event handling and subscriptions for EHR information, intelligent workflow modification and use of Artificial Conversational Entities, according to an embodiment of the system described herein.

Referring to FIG. 12, a system flow diagram 1200 illustrates system functioning in connection with event handling and subscriptions for EHR information, intelligent workflow modification and use of Artificial Conversational Entities. Processing begins at a step 1210 with multiple HIF deployments (which allows the system to capture and integrate patient data, as explained in conjunction with FIG. 1). After the step 1210, processing proceeds to a step 1215, where healthcare professionals or other players are subscribed to patient date, as explained in FIG. 9 and the accompanying text. After the step 1215, processing proceeds to a step 1220, where a new event is generated, as exemplified in FIGS. 6-8. After the step 1220, processing proceeds to a step 1225, where EHR data associated with the new event are posted to an HIF, whereas the event is published to the event bus (see, in particular, FIGS. 6-9 and the associated explanations). After the step 1225, processing proceeds to a test step 1230, where it is determined whether the published new event fits one or more of the currently active subscriptions, i.e. satisfies all filtering conditions of the subscriptions. If so, processing proceeds to a step 1235, where the EHR data associated with the event is delivered to subscribers.

After the step 1235, processing proceeds to a step 1240 (which can be independently reached from the test step 1230 if it was determined that the event does not fit any active subscription), where the patient LHR is analyzed using NLP, as explained in conjunction with FIG. 10. After the step 1240, processing proceeds to a step 1245, where the LHR constructs discovered by the NLP analysis at the previous step 1240 are entered into the ML/AI subsystem for a subsequent analysis and decision-making. After the step 1245, processing proceeds to a test step 1250, where it is determined whether the ML/AI subsystem suggests any workflow modifications, such as an expansion of the current care team illustrated in FIG. 10. If so, processing proceeds to a test step 1255, where it is determined whether the proposed modifications are approved. If so, processing proceeds to a step 1260, where the care workflow is modified.

After the step 1260, processing proceeds to a step 1265, where a patient is admitted for inpatient care. Note that the step 1265 may be independently reached from the test step 1255 if modifications were not approved and from the test step 1250 if workflow modifications were not suggested by the ML/Al subsystem. After the step 1265, processing proceeds to a step 1270, where EHR for the current care phase is generated. After the step 1270, processing proceeds to a step 1275, where an ACE analyzes the current EHR accumulated in LHR records. After the step 1275, processing proceeds to a test step 1280, where it is determined whether conversing with a family of the patient (or other authorized players) is desired at the current phase of cure. If so, processing proceeds to a step 1282, where the ACE chooses a communication venue (as explained in conjunction with FIG. 11), creates a snippet of EHR data for communicating, and converses to the family or other players. After the step 1282, processing proceeds to a step 1285 where the patient is moved to the next care phase. Note that the step 1285 may be independently reached from the test step 1280 if it was determined that there is no need in conversing with the patient's family at the current phase. After the step 1285, processing proceeds to a test step 1290, where it is determined whether the current phase is discharging. If so, processing proceeds to a step 1292, where the ACE assists a healthcare professional in creating a summary of the patient's stay in the hospital. After the step 1292, processing proceeds to a step 1295, where the patient is discharged (with an additional communication with the family, if needed, as explained in FIG. 11). After the step 1295, processing is complete. If it was determined at the test step 1290 that the current phase is not discharging, processing proceeds back to the test step 1270, which may also be reached from the step 1265.

Various embodiments discussed herein may be combined with each other in appropriate combinations in connection with the system described herein. Additionally, in some instances, the order of steps in the flowcharts, flow diagrams and/or described flow processing may be modified, where appropriate. Subsequently, system configurations and functions of the IHF may vary from the illustrations presented herein. Further, various aspects of the system described herein may be implemented using various mobile applications and AAA services and may be deployed on various devices, including, but not limited to smartphones, tablets and other mobile computers. Smartphones may use operating system(s) selected from the group consisting of: iOS, Android OS, Windows Phone OS, Blackberry OS and mobile versions of Linux OS.

Software implementations of the system described herein may include executable code that is stored in a computer readable medium and executed by one or more processors. The computer readable medium may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer readable medium or computer memory on which executable code may be stored and executed by a processor.

The software may be bundled (pre-loaded), installed from an app store or downloaded from a location of a network operator. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of operating a Health Information Framework (HIF) architecture for managing healthcare information, comprising:
receiving, by one or more computing devices, a posting by a first healthcare professional that is a member of a life-long care team for a patient, medical information about the patient in a healthcare information framework;
pushing, by the one or more computing devices and in real time or near real time, the medical information to at least one server that is coupled to a datastore;
analyzing, by the one or more computing devices and using an artificial intelligence (AI) trained to determine whether additional specialists should be added to the life-long care team and subsystems using natural language processing, the medical information to determine whether a second healthcare professional that is not a member of the life-long care team to for the patient is needed to care for the patient;
based on determining that the second healthcare professional is needed, modifying, by the one or more computing devices, a workflow to include the second healthcare professional and
based on the second healthcare professional being included to the life-long care team, causing, by the one or more computing devices, the second healthcare professional to automatically receive the medical information for the patient.

2. The method of claim 1, wherein the first healthcare professional is subject to authorization and appropriate credentials.

3. The method of claim 1, wherein electronic health records provided in the datastore are life-long electronic health records.

4. The method of claim 1, wherein the medical information is filtered based on at least one of: time period, patient ID, event type, and specific parameters or thresholds of data associated with subscribed events.

5. The method of claim 1, further comprising:
a realtime or near realtime event bus receiving an event in response to the medical information being posted by the first healthcare professional, wherein the event bus interacts with the server to cause the second healthcare professional to automatically receive the medical information.

6. The method of claim 5, wherein the medical information corresponds to a data change event.

7. The method of claim 6, wherein the data change event corresponds to arrival of results of a diagnostic laboratory test.

8. The method of claim 5, wherein the medical information corresponds to a new care team event.

9. The method of claim 8, wherein the new care team event is caused by admission of the patient to a healthcare facility.

10. The method of claim 5, wherein the medical information corresponds to a medical appointment event.

11. A non-transitory computer readable medium with instructions stored thereon for operating a Health Information Framework (HIF) architecture for managing healthcare information, that when executed cause a computing system to perform operations comprising:
receiving, by one or more computing devices, a posting by a first healthcare professional that is a member of a life-long care team for a patient, medical information about the patient in a healthcare information framework;
pushing, by the one or more computing devices and in real time or near real time, the medical information to at least one server that is coupled to a datastore;
analyzing, by the one or more computing devices and using an artificial intelligence (AI) trained to determine whether additional specialists should be added to the life-long care team and subsystems using natural language processing, the medical information to determine whether a second healthcare professional that is not a member of the life-long care team to for the patient is needed to care for the patient;
based on determining that the second healthcare professional is needed, modifying, by the one or more computing devices, a workflow to include the second healthcare professional; and
based on the second healthcare professional being included to the life-long care team, causing, by the one or more computing devices, the second healthcare professional to automatically receive the medical information for the patient.

12. The non-transitory computer readable medium of claim 11, wherein the first healthcare professional is subject to authorization and appropriate credentials.

13. The non-transitory computer readable medium of claim 11, wherein electronic health records provided in the datastore are life-long electronic health records.

14. The non-transitory computer readable medium of claim 11, wherein the medical information is filtered based on at least one of: time period, patient ID, event type, and specific parameters or thresholds of data associated with subscribed events.

15. The non-transitory computer readable medium of claim 11, wherein the operations further comprise:
a realtime or near realtime event bus receiving an event in response to the medical information being posted by the first healthcare professional, wherein the event bus interacts with the server to cause the second healthcare professional to automatically receive the medical information.

16. The non-transitory computer readable medium of claim 15, wherein the medical information corresponds to a data change event.

17. The non-transitory computer readable medium of claim 16, wherein the data change event corresponds to arrival of results of a diagnostic laboratory test.

18. The non-transitory computer readable medium of claim 15, wherein the medical information corresponds to a new care team event.

19. The non-transitory computer readable medium of claim 18, wherein the new care team event is caused by admission of the patient to a healthcare facility.

20. The non-transitory computer readable medium of claim 15, wherein the medical information corresponds to a medical appointment event.

21. A computing system for operating a Health Information Framework (HIF) architecture for managing healthcare information comprising:
a memory configured to store instructions;
one or more processors, coupled to the memory, configured to process the stored instructions to:
receive a posting by a first healthcare professional that is a member of a life-long care team for a patient, medical information about the patient in a healthcare information framework;

push, in real time or near real time, the medical information to at least one server that is coupled to a datastore;

analyze, using an artificial intelligence (AI) trained to determine whether additional specialists should be added to the life-long care team and subsystems using natural language processing, the medical information to determine whether a second healthcare professional that is not a member of the life-long care team to for the patient is needed to care for the patient;

based on determining that the second healthcare professional is needed, modify a workflow to include the second healthcare professional; and based on the second healthcare professional being included to the life-long care team, cause the second healthcare professional to automatically receive the medical information for the patient.

22. The computing system of claim 21, further comprising:

a realtime or near realtime event bus configured to receive an event in response to the medical information being posted by the first healthcare professional, wherein the event bus interacts with the server to cause the second healthcare professional to automatically receive the medical information.

* * * * *